United States Patent [19]

Friedman et al.

[11] Patent Number: 5,200,346
[45] Date of Patent: Apr. 6, 1993

[54] ALDICARB IMMUNOASSAY BY SULFONE EQUIVALENTS

[75] Inventors: Stephen B. Friedman, Chapel Hill; Thomas N. Stewart, Durham, both of N.C.

[73] Assignee: Ensys, Inc., Durham, N.C.

[21] Appl. No.: 731,752

[22] Filed: Jul. 16, 1991

[51] Int. Cl.$^5$ ............................................. G01N 33/545
[52] U.S. Cl. ................................. 436/518; 435/7.93; 436/531; 436/538; 436/815
[58] Field of Search ............... 435/7.93; 436/518, 531, 436/538, 815

[56] References Cited

PUBLICATIONS

M. Dong et al., Analysis of Carbamate Pesticides by LC, AEL, 14-27 (Apr. 1990).
R. Bushway and B. Ferguson, Determination of Atrazine, Aldicarb and Methyl-2-Benzimidazolecarbamate Residues in Food by Enzyme Immunoassay (1989) (poster presented at Pacifichem '89, Honolulu, Hawaii, Dec. 17-22, 1989).
N. Andrawes et al., J. Agr. Food Chem., vol. 21, No. 3, pp. 379-386 (1973).
H. Dorough et al., J. Chromatographic Science, vol. 13, pp. 212-224 (1975).
B. Trost et al., J. Org. Chem., 53, 532-537 (1988), Tetra-n-butylammonium Oxone. Oxidations under anhydrous conditions.
J. Hawk et al., Analytical Chemistry, 44, 1315-1317 (1972), Kinetic method for quantitative determination of individual organic peroxides in peroxide mixtures.
J. Brady et al., ACS Symposium Ser., 382 (Biol. Monit. Pestic. Exposure: Meas., Estim., Risk Reduction), 262-284 (1989), Chap. 21, Enzyme immunoassay for aldicarb.

*Primary Examiner*—Mary E. Ceperley
*Attorney, Agent, or Firm*—Bell, Seltzer, Park & Gibson

[57] ABSTRACT

An immunoassay for detecting total aldicarb in an aqueous sample suspected of containing the same is disclosed. In the inventive method, an oxidant is added to the aqueous sample, with the oxidant provided in an amount sufficient to oxidize all aldicarb contained in the solution to aldicarb sulfone. Next, the aqueous sample is combined with a thioether solution capable of neutralizing excess oxidant in the aqueous sample to thereby provide a neutralized test solution. The neutralized test solution is then contacted to an antibody capable of binding aldicarb sulfone, and the aldicarb sulfone bound to the antibody detected.

17 Claims, 1 Drawing Sheet

ALDICARB IMMUNOASSAY BY SULFONE EQUIVALENTS

FIELD OF THE INVENTION

The present invention relates to the testing of toxic pesticides, and particularly relates to the testing of Aldicarb.

BACKGROUND OF THE INVENTION

Aldicarb is a common soil-applied chemical pesticide which has the structure of Formula (I) below:

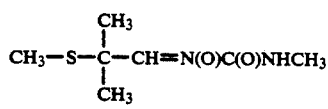
(I)

The IUPAC name for this compound is 2-methyl-2(methylthio)propionaldehyde 0-methylcarbamoyloxime. Once applied to soil it is taken up into plants by the roots, where it protects the plants from certain insects for several weeks. Aldicarb is toxic to humans, so there is a continuing need for methods of testing for its presence in soil, produce, and food products.

Aldicarb lingers in soil. Its persistence in soil, and its oxidation forms in soil, are well known See, e.g., J. Smelt et al., *Pestic. Sci.* 9, 279 (1978). In overview, aldicarb in soil oxidizes first to the sulfoxide shown in formula (II) below, and then to the sulfone shown in formula (III) below.

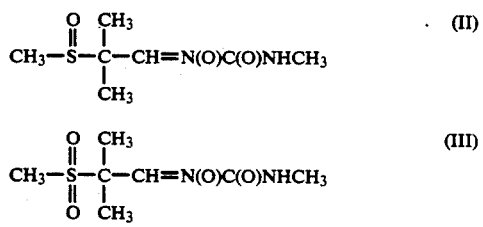

Analytical labs test for the presence of aldicarb in a sample by converting the aldicarb entirely to the sulfone form of Formula (III). Aldicarb concentration can then be reported in "sulfone equivalents". In brief, the aldicarb is converted to the sulfone by reaction with hydrogen peroxide in acetic acid under heat; then extraction of the sulfone into a nonpolar organic solvent; and then injection of the solvent into a high performance liquid chromatography apparatus (HPLC). See generally M. Dong et al., Analysis of carbamate pesticides by LC, *AEL*, 14–27 (Apr. 1990). The advantage of this procedure is its accuracy. The disadvantages, however, are that HPLC equipment is expensive, HPLC equipment is difficult to use, and the total process is time-consuming. Hence, the procedure must be carried out in an analytical laboratory.

It would clearly be desirable to have a procedure which can be carried out in the field, close to the source of potential contamination, so that a rapid indication of aldicarb contamination can be provided. Hence, immunoassays for aldicarb have been developed. See R. Bushway and B. Ferguson, Determination of Atrazine, Aldicarb and Methyl-2-Benzimidazolecarbamate Residues in Food by Enzyme Immunoassay (1989)(poster presented at Pacifichem '89, Honolulu, Hi, Dec. 17–22 1989). The advantage of immunoassays are that they are quick and easy to carry out. The disadvantage of immunoassays are that they employ antibodies, and antibodies bind differently to aldicarb depending on whether it is in its unoxidized, sulfoxide, or sulfone form. The known procedures for converting aldicarb to the sulfone form, however, employ chemicals which either partially or wholly denature antibodies. Hence, there is no immunoassay procedure currently available which measures aldicarb concentration after first converting the aldicarb to sulfone.

In view of the foregoing, objects of the present invention are to provide an aldicarb assay which combines the convenience of an immunoassay, while retaining the accuracy of analytical assays which report aldicarb concentration in sulfone equivalents.

SUMMARY OF THE INVENTION

The present invention provides an immunoassay for detecting total aldicarb in an aqueous sample suspected of containing the same. In the inventive method, an oxidant selected from the group consisting of potassium peroxymonosulfate (Oxone ®, $2KHSO_5 \bullet KHSO_4 \bullet K_2SO_4$) and peroxyacids is added to the aqueous sample, with the oxidant provided in an amount sufficient to oxidize all aldicarb contained in the solution to aldicarb sulfone. Next, the aqueous sample is combined with a thioether solution capable of neutralizing excess oxidant in the aqueous sample to thereby provide a neutralized test solution. The neutralized test solution is then contacted to an antibody capable of binding aldicarb sulfone and the aldicarb sulfone bound to the antibody detected by means such as a homogeneous or heterogenous immunoassay.

BRIEF DESCRIPTION OF THE DRAWINGS

The FIGURE shows the signal given by aldicarb sulfoxide after oxidation to aldicarb sulfone, in an enzyme immunoassay, for different concentrations of aldicarb sulfone after different oxidation times. The concentration of aldicarb sulfoxide is given on the horizontal axis and the immunoassay signal in absorbance units is given on the vertical axis. Oxidization times were six minutes (squares) and twelve minutes (diamonds). Aldicarb sulfoxide was replaced with aldicarb sulfone as a control and incubated six minutes (plus signs) and twelve minutes (triangles).

DETAILED DESCRIPTION OF THE INVENTION

Figure 1:
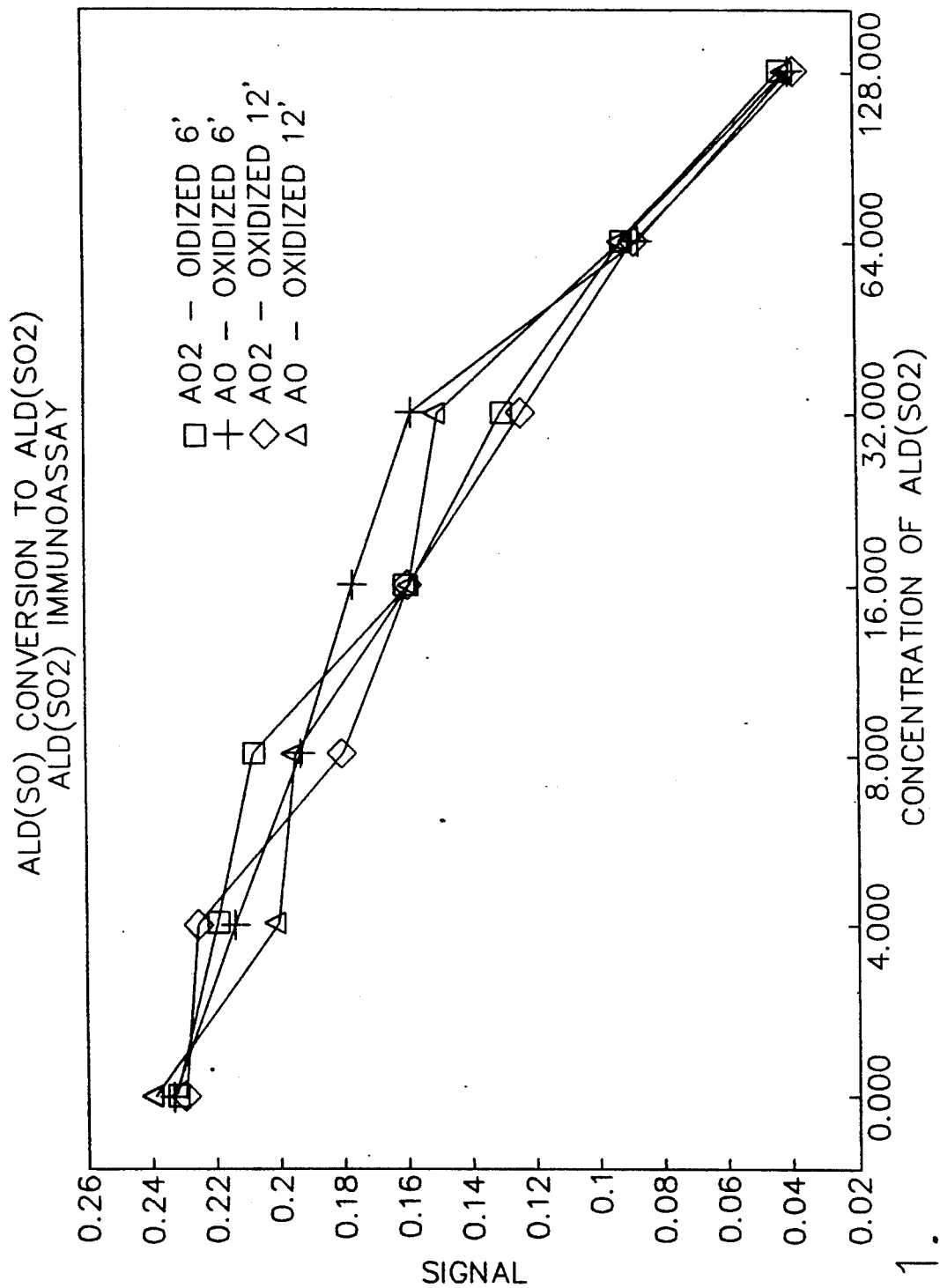

Aqueous samples for testing in the present invention may be obtained from any source suspected of containing aldicarb, such as a soil leachate, runoff, an aqueous extract from a soil sample, and other environmental sources of potentially contaminated water. Fruit and produce may be washed to produce an aqueous sample from the wash solution for testing in accordance with the present invention.

In the inventive method, an oxidant selected from the group consisting of potassium peroxymonosulfate and peroxyacids is added to the aqueous sample, with the oxidant provided in an amount sufficient to oxidize all aldicarb contained in the solution to aldicarb sulfone. Currently preferred oxidants are potassium peroxymonosulfate and peracetic acid. In a particularly preferred embodiment of the present invention, the step of adding oxidant is carried out by adding dry potassium peroxymonosulfate to the aqueous solution, which typically produces an aqueous sample containing from about 2% to about 10% potassium peroxymonosulfate (weight/volume). All reagents are commercially available from a variety of sources.

After adding oxidant, the aqueous sample is combined with a thioether solution capable of neutralizing excess oxidant in the aqueous sample to thereby provide a neutralized test solution. Any thioether capable of oxidation by potassium peroxymonosulfate can be employed in practicing the neutralizing step of the present invention. Currently preferred is 2,2'-thiodiethanol, but any other thioether which (a) can be oxidized to an oxide or sulfone, (b) is water soluble before and after oxidation, and (c) is immunologically distinct from aldicarb, can be used in practicing the present invention. By "immunologically distinct" we mean that antibodies which bind to aldicarb do not bind to the thioether to such an extent that the accuracy of the immunoassay is deleteriously affected. 2,2'-thiodiethanol is commercially available from sources such as the Aldrich Chemical Co. The test solution so produced should have a pH of from 6 to 8, and preferably has a pH of about 7. Ideally, the test solution is an aqueous solution buffered to a pH of from about 6.5 to about 7.5.

Once the aqueous sample has been neutralized, the neutralized test solution is contacted to an antibody capable of binding aldicarb sulfone and the aldicarb sulfone bound to the antibody detected by means such as a homogeneous or heterogenous immunoassay. For example, the detecting step may be carried out by combining the test solution with a solution comprising aldicarb sulfone conjugated to a detectable group prior to the contacting step; then, after the contacting step, removing the antibodies from the potassium peroxymonosulfate solution; and then detecting the presence or absence of the detectable group bound to the antibodies. Alternatively the detecting step may be carried out by removing the antibodies from the test solution; then contacting the antibodies to a solution containing aldicarb sulfone conjugated to a detectable group; and then detecting the presence or absence of the detectable group bound to the antibodies.

In addition to the scientific and technical literature which may be referenced to facilitate the practice of the present invention, with which those skilled in the art will be well familiar, there are also numerous patent references available which concern immunometric assays. A few examples of there references are Skold et al. U.S. Pat. No. 4,727,022 titled "Methods for Modulating Ligand-Receptor Interactions and their Application," Forrest et al. U.S. Pat. No. 4,659,678 titled "Immunoassay of Antigens," David et al. U.S. Pat. No. 4,376,110, titled "Immunometric Assays Using Monoclonal Antibodies," Litman et al. U.S. Pat. No. 4,275,149, titled "Macromolecular Environment Control in Specific Receptor Assays," Maggio et al. U.S. Pat. No. 4,233,402, titled "Reagents and Method Employing Channeling," and Boguslaski et al. U.S. Pat. No. 4,230,767 titled "Heterogenous Specific Binding Assay Employing a Coenzyme as Label". Applicants specifically intend that the disclosures of these references be incorporated herein by reference.

The present invention is explained in greater detail in the following non-limiting examples. In these examples, μg means micrograms, ml means milliliters, M means Molar, PBS means phosphate buffered saline, HRP means horseradish peroxidase, μl means microliters, BTG means bovine thyroglobulin, DMF means dimethyl formamide, TEA means triethylamine, IBCF means isobutylchloroformate and temperatures are given in degrees centigrade unless otherwise indicated.

EXAMPLE 1

Preparation of Aldicarb Sulfone-BTG Immunogen

Aldicarb oxime (256 mg) is dissolved in five ml of toluene. One drop of triethylamine is added, followed by five ml of chloroform containing ethyl isocyanatoacetate (280 mg). The reaction mixture is warmed to 48 degrees and incubated for two and a half hours. The solvent is removed using a rotary evaporator yielding the aldicarb acetate ethyl ester, as shown below:

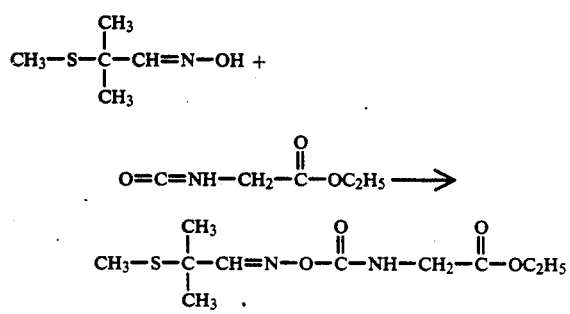

The resulting aldicarb acetate ethyl ester intermediate (210 mg) is then dissolved in 20 ml of water containing 30 mg/ml of sodium carbonate. The solution is incubated at room temperature for 30 minutes after which all the ester has been hydrolyzed to the free acid. The methanol is removed by rotary evaporation, the aqueous solution is acidified with HCl and the product extracted into ethyl acetate. The aldicarb acetate (72 mg) is dissolved in 2 ml of methanol, to which is added 133 mg of 32% peracetic acid in one ml of methanol (3 ml final volume). The solution is incubated for 30 minutes at room temperature, and dried by rotary evaporation to produce the aldicarb acetate sulfone:

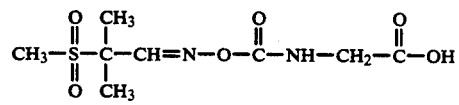

The aldicarb acetate sulfone (36 mg) is then dissolved in one ml of DMF, with the resulting solution chilled in a NaCl/water ice bath. TEA (17 μl) is added followed by 16 μl of IBCF. After one minute, the precipitate is spun down in a microfuge and the supernatant is added in four aliquots to 4 ml of 200 mM sodium carbonate, pH 8.8 containing 150 mg of bovine thyroglobulin. The reaction mixture is incubated at 4 degrees for 12 hours. The conjugate is then purified by placing the reaction mixture in a dialysis bag and dialyzing against one liter of PBS with four changes of buffer.

EXAMPLE 2

Preparation of Monoclonal Antibodies

Female Balb/c mice (Charles River Laboratories, Raleigh, N.C.) were immunized subcutaneously with 50 μg of aldicarb-BTG conjugate prepared as described in Example 1 above mixed with adjuvant (MPL + TDM Emulsion, RIBI Immunochem Research, Inc., Hamilton, VT.). Subcutaneous booster injections (25 μg) were given at day 21, day 35, and then on a monthly basis until the detection of a serum response. The mouse sera were tested by enzyme-linked immunosorbent assay (ELISA) 5 days after each boost for titer and free hapten dose response. Mice responding to the immunization protocol were given a final intraperitoneal injection (25 μg, no adjuvant) three days before using their splenocytes for hybridoma fusion.

The mouse sera and hybridoma supernatants were tested by ELISA (E. Engvall and P. Perlman, *Immunochemistry* 8, 871 (1971), according to the following protocol. Microtiter plates were coated overnight at 4° C. with an appropriate aldicarb conjugate in carbonate buffer (pH 9.6). The plates were washed between each step with PBS-Gel. The plates were blocked for 30 minutes with PBS-gel and incubated with antisera or supernatant for an additional 30 minutes. Goat antimouse IgG + IgM conjugated to horseradish peroxidase (KPL, Gaithersburg, Md.) was added for 30 minutes followed by the initiation of the enzyme reaction with TMBS substrate (KPL, Gaithersburg, Md). The reaction was stopped 5 minutes later by the addition of $H_2SO_4$. For the inhibition assay, free aldicarb derivatives were mixed with antisera and transferred to antigen-coated plates and the test was performed as described above.

The production of monoclonal antibodies was performed according to Fenderson et al., (Dev. Biol 103:117-128, 1984). All cultures of hybridomas and SP2/0 (American Type Culture Collection, Rockville, Md.D) cells were grown in Dulbeccco-Modified Eagle's Medium supplemented with 20% Fetal Bovine Serum (Gibco Laboratories, Grand Island Biological Co., Grand Island, N.Y). Splenocytes were fused with SP2/0 cells in a 5:1 ratio and plated into 96 well-culture plates at a density of $1.5 \times 10^5$ cells per well. HAT was added to the media 24 hrs later to select for hybridomas. Hybridomas recognizing fee aldicarb were cloned twice by limiting dilution.

EXAMPLE 3

Preparation of Aldicarb-Horseradish Peroxidase (HRP) Conjugate

Succinic anhydride (100 mg) is dissolved in one ml of acetonitrile. Aldicarb oxime sulfone (166 mg) is dissolved in 2 ml of ethyl acetate:acetonitrile (1:1). The two solutions are combined and TEA (65 μl) is added and the reaction mixture is incubated at room temperature for 5 hours. The solvent is removed with a stream of nitrogen to obtain the colorless oily aldicarb sulfone succinate:

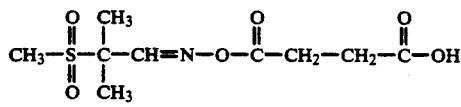

Aminopropyl-HRP (AP-HRP) is then prepared by first dissolving 19.5 mg of HRP in 1.0 ml deionized water and adding 200 μl of 40 mg/ml sodium periodate in water. Incubate at room temperature for 20 minutes and purify the oxidized HRP on a PD-10 column (Pharmacia) into 200 mM sodium carbonate, pH 8.8. The HRP is collected in a total volume of 1.6 ml to which is added 250 μl of 7.4 mg/ml diaminopropane (DAP) ($H_2N-CH_2-CH_2-CH_2-NH_2$) in carbonate buffer. Incubate one hour at room temperature and add 200 μl of 17 mg/ml sodium borohydride to form a stable DAP-HRP derivative. Incubate for 90 minutes at 4 degrees. Place the mixture in a dialysis bag and purify the AP-HRP by dialyzing against PBS (one liter with four changes) to remove borohydride and excess DAP.

The aldicarb-HRP conjugate is then prepared by first diluting 300 μl of the AP-HRP made above with 300 μl of 200 mM carbonate buffer, pH 8.9. Aldicarb sulfone succinate (7.4 mg) is dissolved in 120 μl of DMF, then 2.2 μl of TEA and 2.0 μl of IBCF is added for one minute. Next, 30 μl of mixed anhydride solution is added to the AP-HRP solution and is incubated at room temperature for 70 minutes. This "mixed anhydride method" produces the conjugate:

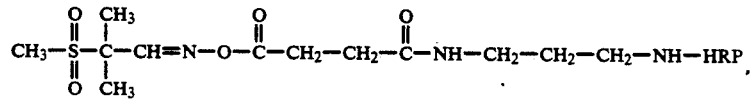

Purification is accomplished on a PD-10 column; the solution is collected in PBS in a volume of one ml. The aldicarb-DAP-HRP conjugate is then purified by dialysis into phosphate-buffered saline (PBS).

EXAMPLE 4

Oxidation of Aldicarb with Potassium Peroxymonosuslfate

To a 1 ml sample of water containing either no aldicarb sulfoxide (control) or aldicarb sulfoxide in an amount of 4, 8, 16, 32, 64, or 128 parts per billion is added dry particulate potassium peroxymonosulfate obtained from the Aldrich Chemical Company (1001 West Saint Paul Avenue, Milwaukee, Wis. 53233 USA) to provide a 5% (weight/volume) potassium peroxymonosulfate solution. Each solution is allowed to incubate from 6 to 12 minutes at room temperature to allow complete conversion of the aldicarb sulfoxide to the aldicarb sulfone.

EXAMPLE 5

Neutralization of Excess Potassium Peroxymonosulfate with Thioether

To a potassium peroxymonosulfate solution prepared as described in Example 4 above is added 17 μl of 2,2'-thiodiethanol (obtained from Aldrich Chemical Co.) in 170 μl of 1 M $Na_3PO_4$. This step neutralizes the excess potassium peroxymonosulfate and raises the pH of the solution to about 7.0, making the solution immunoassay-compatible. The potassium peroxymonosulfate solution is incubated about 5 minutes to insure neutralization of excess potassium peroxymonosulfate.

EXAMPLE 6

Immunoassay of Aldicarb Sulfone

100 μl of each neutralized potassium peroxymonosulfate solution, prepared as described in Example 5 above, is mixed with 100 μl of solution containing an aldicarb sulfone-horseradish peroxidase conjugate. 100 μl of the resulting solution is added to a microtiter plate having anti-aldicarb sulfone antibodies immobilized therein.

The microtiter plate is then incubated for one hour, the well washed with PBS containing 0.05% gelatin, 100 μl of HRP substrate is added (2 mg/ml o-phenylenediamine in 0.1 M citrate buffer with 0.02% $H_2O_2$), and color development stopped after ten minutes of incubation by adding 100 μl of 1M $H_2SO_4$. Color development in absorbance units is then measured on a microtiter plate reader at 490 nanometers. Results are shown in the FIGURE.

The foregoing examples are illustrative of the present invention, and are not to be construed as limiting thereof. The invention is defined by the following claims, with equivalents of the claims to be included therein.

That which is claimed is:

1. An immunoassay for detecting total aldicarb in an aqueous sample suspected of containing the same, comprising:
    adding an oxidant selected from the group consisting of potassium peroxymonosulfate and peroxyacids to the aqueous sample, the oxidant provided in an amount sufficient to oxidize all aldicarb contained in said solution to aldicarb sulfone; then
    combining the aqueous sample with a thioether solution capable of neutralizing excess oxidant in said aqueous sample to thereby provide a neutralized test solution; then
    contacting the neutralized test solution to an antibody capable of binding aldicarb sulfone; and then
    detecting the aldicarb sulfone bound to the antibody.

2. A method according to claim 1, wherein said combining step is carried out by combining the aqueous sample with an aqueous thioether-containing solution.

3. A method according to claim 1, wherein said test solution has a pH of from 6 to 8.

4. A method according to claim 1, wherein said combining step is carried out by combining the potassium peroxymonosulfate solution with an aqueous thioether-containing solution, and wherein said test solution is buffered to a pH of from about 6.5 to about 7.5.

5. A method according to claim 1, wherein said step of adding oxidant is carried out by adding dry potassium peroxymonosulfate to the aqueous solution.

6. A method according to claim 1, wherein said adding step produces an aqueous sample containing from about 2% to about 10% potassium peroxymonosulfate (weight/volume).

7. A method according to claim 1, wherein said thioether is 2,2'-thiodiethanol.

8. A method according to claim 1, wherein said detecting step comprises an immunoassay selected from the group consisting of heterogenous and homogenous immunoassays.

9. A method according to claim 1, wherein said detecting step is carried out by:
    combining said test solution with a solution comprising aldicarb sulfone conjugated to a detectable group prior to said contacting step; then, after said contacting step,
    removing said antibodies from said test solution; and then
    detecting the presence or absence of said detectable group bound to the antibodies.

10. A method according to claim 1, wherein said detecting step is carried out by:
    removing said antibodies from said test solution; then
    contacting said antibodies to a solution containing aldicarb sulfone conjugated to a detectable group; and then
    detecting the presence or absence of said detectable group bound to the antibodies.

11. An immunoassay for detecting total aldicarb in an aqueous sample suspected of containing the same, comprising:
    adding dry potassium peroxymonosulfate to the aqueous sample, the potassium peroxymonosulfate provided in an amount sufficient to oxidize all aldicarb contained in said solution to aldicarb sulfone; then
    combining the aqueous sample with an aqueous thioether-containing solution capable of neutralizing excess oxidant in said aqueous sample to thereby provide a neutralized test solution having a pH of from 6 to 8; then
    contacting the neutralized test solution to an antibody capable of binding aldicarb sulfone; and then
    detecting the aldicarb sulfone bound to the antibody.

12. A method according to claim 11, wherein said test solution is buffered to a pH of from about 6.5 to about 7.5.

13. A method according to claim 11, wherein said adding step produces an aqueous sample containing from about 2% to about 10% potassium peroxymonosulfate (weight/volume).

14. A method according to claim 11, wherein said thioether is 2,2'-thiodiethanol.

15. A method according to claim 11, wherein said detecting step comprises an immunoassay selected from the group consisting of heterogenous and homogenous immunoassays.

16. A method according to claim 11, wherein said detecting step is carried out by:
    combining said test solution with a solution comprising aldicarb sulfone conjugated to a detectable group prior to said contacting step; then, after said contacting step,
    removing said antibodies from said test solution; and then
    detecting the presence or absence of said detectable group bound to the antibodies.

17. A method according to claim 11, wherein said detecting step is carried out by:
    removing said antibodies from said test solution; then
    contacting said antibodies to a solution containing aldicarb sulfone conjugated to a detectable group; and then
    detecting the presence or absence of said detectable group bound to the antibodies.

* * * * *